United States Patent [19]

Baudouin

[11] 3,954,888
[45] May 4, 1976

[54] PROCESS FOR THE PREPARATION OF 2-PHENYL-ETHANOL

[75] Inventor: Michel Baudouin, St. Fons, France

[73] Assignee: Rhone-Poulenc Textile, Paris Cedex, France

[22] Filed: Jan. 9, 1975

[21] Appl. No.: 539,626

[30] Foreign Application Priority Data
Jan. 11, 1974   France .............................. 74.00985

[52] U.S. Cl. ............................ 260/618 R; 260/487
[51] Int. Cl.² ........................................ C07C 29/00
[58] Field of Search ....................... 260/487, 618 R

[56] References Cited
OTHER PUBLICATIONS

Ichikawa et al., *J.A.C.S.*, Vol. 80, pp. 6005–6009 (1958).
Ichikawa et al., *Tetrahedron*, Vol. 22, pp. 407–413 (1966).
McKillop et al., *J.A.C.S.*, Vol. 93(19), pp. 4841–4844 (1971).
McKillop et al., *Chem. Brit.*, Vol. 9,(1), pp. 4–11 (1973).

*Primary Examiner*—James O. Thomas, Jr.
*Assistant Examiner*—James H. Reamer
*Attorney, Agent, or Firm*—Cushman, Darby & Cushman

[57] ABSTRACT

A process for preparing 2-phenyl-ethanol is provided in which ethylene is reacted with benzene and thallic trifluoroacetate in trifluoroacetic acid as the solvent to give 2-phenyl-ethyl trifluoroacetate which is then converted, in known manner, into 2-phenyl-ethanol.

7 Claims, No Drawings

PROCESS FOR THE PREPARATION OF 2-PHENYL-ETHANOL

The present invention relates to a process for preparing 2-phenyl-ethanol.

2-Phenyl-ethanol is one of the most widely used materials in the perfume industry. In order to have large amounts of this compound available, it is desirable to increase the number of ways of obtaining it, using reagents which are both inexpensive and as varied as possible.

K. Ichikawa et al., *Tetrahedron*, 22, pages 407 to 413 (1966) have described a method for preparing a homologue of 2-phenyl-ethanol, namely 2-(p-methoxyphenyl)-ethanol, as its acetic acid ester, which comprises reacting ethylene with methoxybenzene and thallic acetate in the presence of perchloric acid in acetic acid. Under these conditions, the expected product, namely 2-(p-methoxy-phenyl)-ethyl acetate, is obtained in a yield not exceeding 3%, most of the remainder consisting of ethylene glycol diacetate. It has been discovered that this process is not applicable when methoxy-benzene is replaced by benzene, and, moreover, it has been found, surprisingly, according to the present invention, that by using a solution of thallic trifluoroacetate in trifluoroacetic acid, instead of a solution of thallic acetate in acetic acid in the presence of a strong protonic acid, it is possible to prepare 2-phenyl-ethanol, via its trifluoroacetic acid ester, in a much higher yield than that mentioned by K. Ichikawa et al.

According to the present invention, there is provided a process for preparing 2-phenyl-ethanol, which comprises (a) reacting ethylene with benzene and thallic trifluoroacetate in trifluoroacetic acid as solvent, and (b) converting, in known manner the 2-phenyl-ethyl trifluoroacetate which is formed in step (a) into 2-phenyl ethanol.

Step (a) of the process which gives 2-phenylethyl trifluoroacetate can be illustrated overall by the following equation:

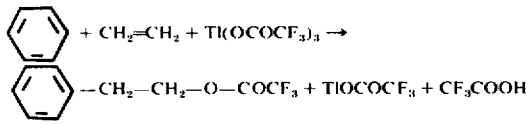

The amount of ethylene employed, expressed as the number of moles of ethylene per $Tl^{3+}$ gram ion, can be approximately stoichiometric or can be non-stoichiometric, without disadvantage. For example, the amount of ethylene used can be greater or slightly less than the stoichiometric requirement.

The amount of benzene employed, expressed as the number of moles of benzene per $Tl^{3+}$ gram ion, can be identical to or different from the amount of ethylene employed, and can vary within wide limits. It is possible to use amounts which are approximately stoichiometric, although it is possible to depart from this value in either direction; amounts which are markedly greater than the stoichiometric requirements have been found particularly suitable.

The trifluoroacetic acid used is usually the anhydrous pure product, but it is also possible to employ trifluoroacetic acid containing not more than, say, 5%, preferably not more than 2%, by weight of water. The amount of acid employed can vary within wide limits, although the amount must, in general, be sufficient to dissolve the thallic salt employed; there is no upper limit and the acid can be used as a diluent.

The process of the present invention can, for example, be carried out as follows, a mixture of benzene and trifluoroacetic acid is introduced into a suitable reactor and heated to the desired temperature. Ethylene is then introduced, either at atmospheric pressure or at a higher pressure, contact between the ethylene and the reaction mixture being effected by any known means. A solution of thallic trifluoroacetate in trifluoroacetic acid is then added to the reactor and contact with ethylene is maintained until the $Tl^{3+}$ ions have been converted completely to $Tl^+$ ions.

As a variant, it is possible to introduce all the components other than ethylene directly into the reactor, and then to establish contact with the ethylene until the $Tl^{3+}$ ions have disappeared. This disappearance of $Tl^{3+}$ ions can be verified by treating a sample of the mixture with excess sodium hydroxide; if no $Tl^{3+}$ ions are present no precipitate of thallic oxide occurs.

Step (a) of the reaction is generally carried out at a temperature of $-10°$ to $60°C$, preferably $0°$ to $40°C$.

The unreacted trifluoroacetic acid and the benzene can be removed from the reaction mixture by any suitable means, for example by distillation, before carrying out step (b) of the reaction.

Conversion of 2-phenyl-ethyl trifluoroacetate to 2-phenyl-ethanol can be effected by any known method, for example by alcoholysis or saponification of the ester group. Whatever the process adopted the trifluoroacetic acid ester can be isolated beforehand from the mixture formed at the end of step (a) or, preferably, can be treated directly in situ to give 2-phenyl-ethanol which is isolated from the alcoholysis or saponification reaction mixture in the usual way.

The reduced thallium salt present in the residual solutions resulting from the treatment can optionally be recovered, before step (b), by precipitation employing a suitable anti-solvent. The thallous derivative can be treated to regenerate thallic ions, for example by chemical or electrochemical oxidation.

The following Example further illustrates the present invention.

EXAMPLE 50 g (0.64 mol) Of benzene and 50 g of trifluoroacetic acid are introduced into a 500 cm³ glass reactor equipped with a stirring system, a thermometer, a dropping funnel and an external cooling device and which is connected to a source of ethylene at atmospheric pressure. The mixture obtained is cooled to about 4°C and ethylene is introduced into the apparatus whilst stirring is started. A solution of 48 g (0.088 mol) of thallic trifluoroacetate in 122.8 g of trifluoroacetic acid is then added gradually over 1 hour 10 minutes to the contents of the reactor. When the addition is complete, the reaction mixture is left in contact with the ethylene for a further 15 minutes until the $Tl^{3+}$ ions have completely disappeared (verified by the absence of a precipitate of thallic oxide when a sample of the mixture is treated with excess sodium hydroxide). The trifluoroacetic acid and most of the residual benzene are then removed by distillation under reduced pressure. The oily residue obtained is washed with 150 cm³ of diethyl ether to precipitate thallous trifluoroacetate which is subsequently filtered off.

The filtrate is concentrated by evaporation under reduced pressure and then 95 cm³ of an aqueous sodium hydroxide solution containing 20% by weight of pure base are added to it and then the whole is boiled for 15 minutes. After cooling, the product resulting from the saponification process is extracted with three times 200 cm³ of diethyl ether. The ether extracts are combined, dired over anhydrous sodium sulphate and concentrated by evaporation under reduced pressure. The yield of 2-phenyl-ethanol, relative to the thallic salt introduced, is 34% as determined by vapour phase chromatographic analysis.

I claim:

1. In a process for the preparation of 2-phenyl-ethanol which comprises:
   a. reacting ethylene with benzene and a metallic carboxylate in a strong protonic acid as solvent to form a 2-phenyl-ethyl carboxylate and
   b. converting the 2-phenyl-ethyl carboxylate into 2-phenyl-ethanol;
   the improvement which comprises reacting ethylene with benzene and thallic trifluoroacetate in the presence of trifluoroacetic acid at a temperature of −10° to 60°C.

2. Process according to claim 1, wherein approximately 1 mole of ethylene is employed per $Tl^{3+}$ gram ion.

3. Process according to claim 1, wherein approximately 1 mole of benzene is employed per $Tl^{3+}$ gram ion.

4. Process according to claim 1, wherein more than 1 mole of benzene is employed per $Tl^{3+}$ gram ion.

5. Process according to claim 1, wherein the trifluoroacetic acid contains at most 5% by weight of water.

6. Process according to claim 1, wherein step (a) is carried out at a temperature from 0° to 40°C.

7. Process according to claim 1, wherein step (b) is carried out directly in situ in the reaction mixture obtained from step (a) by alcoholysis or saponification.

* * * * *

UNITED STATES PATENT OFFICE
CERTIFICATE OF CORRECTION

Patent No. __3,954,888__   Dated __May 4, 1976__

Inventor(s) __Michel Baudouin__

It is certified that error appears in the above-identified patent and that said Letters Patent are hereby corrected as shown below:

In the heading:

Change the name of the assignee from "Rhone-Poulenc Textile" to --Rhone-Poulenc Industries--

Signed and Sealed this

Fifteenth Day of March 1977

[SEAL]

Attest:

RUTH C. MASON
*Attesting Officer*

C. MARSHALL DANN
*Commissioner of Patents and Trademarks*